US005290421A

United States Patent [19]

Reynolds et al.

[11] Patent Number: 5,290,421

[45] Date of Patent: Mar. 1, 1994

[54] OXYGEN SENSOR LEAD WIRE

[75] Inventors: Kim A. Reynolds, Berwyn, Pa.; Joseph A. Williams, III, Chagrin Fall, Ohio

[73] Assignee: Markel Corporation, Norristown, Pa.

[21] Appl. No.: 757,833

[22] Filed: Sep. 11, 1991

[51] Int. Cl.[5] .............................................. G01N 27/26

[52] U.S. Cl. .................................... 204/424; 204/427; 204/428

[58] Field of Search ........................ 204/424, 427, 428

[56] References Cited

U.S. PATENT DOCUMENTS 4,127,464 11/1978 Ichikawa et al. .................... 204/428
4,566,950 1/1986 Miles .................................... 204/435
4,897,174 1/1990 Wang et al. .......................... 204/428
4,948,491 8/1990 Kato et al. ........................... 204/428
5,073,247 12/1991 Weyl .................................... 204/428
5,139,639 8/1992 Holleboom ........................... 204/428

*Primary Examiner*—John Niebling
*Assistant Examiner*—Bruce F. Bell
*Attorney, Agent, or Firm*—Synnestvedt & Lechner

[57] ABSTRACT

Disclosed is an oxygen sensor and lead wire therefor. The lead wire has a first end contained within the oxygen sensor and a second end outside the oxygen sensor, the lead wire comprising an electrically insulating wall portion having passage means for providing enhanced fluid communication between the interior of the sensor and the exterior thereof. According to preferred embodiments, such passage means comprises a bore or a passageway in the insulating wall portion.

15 Claims, 3 Drawing Sheets

60
52a
52b
63
61
62

OXYGEN SENSOR LEAD WIRE

This invention relates to apparatus for determining the concentration of oxygen in gaseous materials, and more particularly to lead wire used in apparatus for the determination of oxygen content in the exhaust gas of internal combustion engines.

Internal combustion engines, and particularly automotive type internal combustion engines, produce exhaust gases which include carbon monoxide, unburned or partially burned hydrocarbons and nitrogen oxides. These materials are undesirable byproducts of the combustion process, and their presence in the exhaust gases can be substantially reduced by proper control of combustion conditions. One condition which is important in establishing efficient combustion and hence reduced levels of pollutants in the exhaust gas is the amount of air provided to the combustion process. The amount of air introduced into the combustion chamber is frequently controlled by systems which first require determining the oxygen content in the exhaust gas. This information is then utilized to control the respective amounts of fuel and air being supplied to the engine so that the exhaust gases will have the desired composition. Thus, electrochemical sensors have heretofore frequently been used as part of electrical systems in automobiles for measuring and controlling the composition of exhaust gases.

Such sensors typically utilize a solid electrolyte to determine the oxygen concentration in the exhaust gases. The electrolyte typically comprises an oxygen-ion-conductive tube or cone having an electrode on the outer and inner surfaces thereof. The outer surface of the sensor is exposed to the exhaust gases and the interior of the sensor is provided with a reference source of oxygen, such as ambient air. In operation, the differential in oxygen concentration between the exhaust gases and the reference source causes conduction of oxygen ions through the ion-conductive body, resulting in an electrical current which is dependent upon the relative content of oxygen in the exhaust gas and the reference source.

In order to fully activate the solid electrolyte of such sensors and to obtain an appreciable output voltage for measuring oxygen concentration, the sensor element must be heated to an elevated temperature. It has frequently been common practice to rely upon the heat of the exhaust gases passing over the outer electrode to cause the necessary increase in the temperature of the sensor element. However, this procedure has several drawbacks. For example, such arrangements result in a sensor that is essentially inoperative, or only marginally operative, during the warm-up period of the internal combustion engine; yet, it is during this warm-up period that the concentration of pollutants in the exhaust gases is the highest. In order to overcome this disadvantage, it has been proposed to provide the oxygen sensor with an electrical heating element for rapidly increasing the temperature of the sensor. Such heated oxygen sensors are disclosed, for example, in U.S. Pat. Nos. 4,169,778; 4,175,019; 4,178,222; and 4,897,174.

In each of the apparatus described in the above-listed patents, a shell or outer casing encloses the heating element and the inner electrode. This shell is typically provided with holes, gaps or the like which provide a source of sufficient ambient air for the inner electrode. Such an arrangement, however, also has disadvantage. For example, the relatively large holes and gaps in the shell of the sensor tend to encourage conductive cooling of the sensor element, thereby lengthening the time required to heat the sensor. Furthermore, gaps and openings in the shell or casing tend to allow undesirable penetration of contaminants or other potentially deactivating substances into the interior of the sensor element, thereby potentially interfering with effective operation of the device.

It has thus been proposed that the operation of heated oxygen sensors can be improved by providing such sensors with a casing or shell which provides a substantially hermetic seal around the elements of the oxygen sensor. While such a seal overcomes the disadvantages described above, it creates further difficulties. For example, it becomes increasingly difficult to provide the inner electrode of the oxygen sensor with a proper reference source of oxygen. Thus, a need has arisen in the art to provide a heated oxygen sensor which is at once substantially hermetically sealed from the environment but which provides an adequate flow of reference oxygen to the inner electrode thereof.

SUMMARY OF THE INVENTION

The above-noted disadvantages of the prior art are overcome and the needs thereof are satisfied by providing oxygen sensor lead wire according to the present invention. In particular, the present invention provides lead wire of a type which is especially suited for an oxygen sensor comprising a substantially closed container, preferably a substantially hermetically closed container. The electrically conductive lead wire, which typically has a first end contained within the container and a second end outside the container comprises an electrically insulating wall portion having passage means for providing enhanced fluid communication between the interior of the container and the exterior of the container. Applicants have found that lead wire according to the present invention provides an adequate flow of reference oxygen to the inner electrode while allowing the interior elements of the sensor, preferably including a heater therefore, to be substantially otherwise hermetically isolated from ambient conditions.

DESCRIPTION OF PREFERRED EMBODIMENTS

Figure 1:
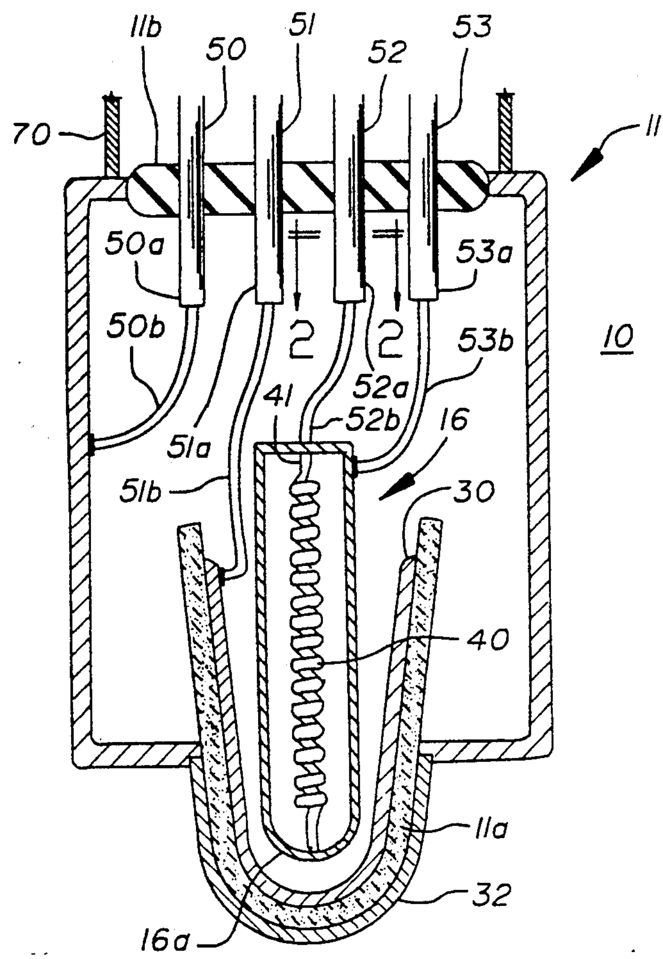
FIG. 1 is a semi-schematic view showing the arrangement of the oxygen sensor elements according to one embodiment of the present invention.

The present invention provides oxygen sensors, and preferably heated oxygen sensors, in which at least a portion of the elements thereof are mounted or otherwise contained within a closed container. According to certain preferred embodiments, the closed container is a substantially hermetically closed container. As used herein, the term "closed container" refers to a housing or vessel having walls which, in a gaseous environment such as air, provide a space inside the container which is substantially separate from the space surrounding the container. For the purposes of convenience, the space surrounding such a closed container will sometimes be referred to herein as exterior space and the space within such container will sometimes be referred to as interior space.

It will be appreciated by those skilled in the art that most modern materials of construction and methods of joining such materials have some degree of permeability to air. Thus, the term "substantially hermetically closed" is used herein in a relative sense to represent a degree of air tightness which is large compared to containers which have passages, openings or gaps in the walls thereof for the purpose of allowing fluid communication between the interior space and the exterior space. Thus, it is contemplated that the exact degree of separation or isolation provided by the closed containers of the present invention will vary widely. That is, closed containers which are not substantially hermetically closed will more readily admit ambient air into the interior space thereof than will a substantially hermetically closed container. Furthermore, it is to be understood that the term "hermetically closed" refers to the condition of the container in the absence of the fluid communication means incorporated in the lead wire of the present invention. It is generally preferred, therefore, that the closed container of the present invention be substantially hermetically closed and that fluid communication between the interior space and the exterior space be provided substantially only by the lead wire of the present invention.

Techniques for manufacturing and producing closed containers of the present invention, including substantially hermetically closed containers, are well known to those skilled in the art, and all such techniques are readily adaptable for use according to the present invention. Furthermore, it is contemplated that the materials of construction of the closed container will also vary widely and that numerous diverse materials may be joined by known methods to provide a closed container. For example, it is contemplated that metals, such as copper, stainless steel, platinum and brass, and plastics and ceramics may be brought together in known fashion to form a closed container, and all such closed containers are within the scope of the present invention.

A portion of the wall of the closed container preferably comprises oxygen-ion-conductive material, and even more preferably a ceramic oxygen-ion-conductive material. Oxygen-ion-conductive materials are well-known in the art and all such materials are within the scope of the invention. It is contemplated, however, that the oxygen-ion-conductive material of the present invention will frequently comprise zirconium oxide, including stabilized forms of zirconium oxides. It is also contemplated that the wall portion of the closed container which comprises such ion-conductive material may be formed into a large variety of shapes, such as tubes, cones and plates. All such shapes are within the scope of the present invention.

The ion conductive wall portion of the closed container also preferably contains electrodes on at least a portion of the inner and outer surfaces thereof. As explained hereinabove, operation of the present sensors produces an electrical potential between the two electrodes. In automobile applications, this potential difference constitutes an input to the pollution control system. As an aid in communicating the sensed information to the control system, the inner and outer electrodes each preferably include a terminal or a terminal portion for facilitating establishment of electrical contact with the lead wire. It is contemplated that numerous types of electrodes and terminals are suitable for use according to the present invention. In general, however, the electrodes will generally comprise a thin film platinum electrode. Methods of forming wall portions having such electrodes are well-known in the art.

The present oxygen sensors preferably include a heating element, and even more preferably an electrical resistance heating element, for rapidly increasing the temperature of the sensor. The heating element is preferably contained within the closed container of the present invention. It will be apparent to those skilled in the art that enclosing the heating element within the closed container maximizes the ability of the sensor to independently reach optimum operating temperature. It is contemplated that numerous and varied heating elements are adaptable for use according to the present invention, and all such heating elements are within the scope hereof. Such heating elements and the methods of their manufacture are well known in the art. Exemplary heating elements adaptable for use in oxygen sensors are described in U.S. Pat. No. 4,178,222, which is incorporated herein by reference.

An important and critical aspect of the present invention resides in the provision of lead wires of the type described herein. In particular, difficulties arise in the operation of oxygen sensors having inner electrodes and/or heating elements contained in substantially closed containers. For example, the provision of such substantially closed containers, and especially substantially hermetically closed containers, significantly reduces the amount of reference oxygen available to the inner electrode. Furthermore, because there is relatively little ambient air available to the inner electrode, there is an increased likelihood that small amounts of gaseous contaminants found within the closed container will deleteriously effect operation of the sensor.

Thus, the present lead wire comprises means for transmitting electrical signals therethrough and an insulating cover surrounding a substantial portion of the electrical signal conducting means, the cover including means therein or thereon for enhancing fluid communication between the interior space of the closed container and the exterior space. The preferred oxygen sensors of the present invention thus comprise a closed container and a lead wire for the oxygen sensor, said lead wire having a first end disposed within said closed container and a second end in the exterior space of said closed container. In this way, a source of reference gas, such as ambient air, can be provided to the interior of the closed container.

Although it is contemplated that lead wires of all lengths are adaptable for use according to the present invention, it is contemplated that a particular advantage can be obtained with lead wires of increased length. That is, the lead wire of the present invention permits configurations in which the reference gas made available to the inner electrode is sampled from a location which is remote relative to the oxygen gas sensor. The capacity to obtain such remote sensing has distinct advantages. For example, the ambient air immediately surrounding an automobile exhaust manifold may be relatively highly contaminated with pollutants or other contaminants which would undesirably alter the concentration of oxygen in the reference gas. Thus, the lead wire of the present invention will preferably have extended lengths, that is, lengths of greater than about 12 inches, such that the source of reference gas is sampled from a location which is relatively remote from the actual oxygen sensor. It is contemplated, for example, that the exterior end of the lead wire may extend to the main engine compartment of an automobile. In this way, it is possible for the lead wire to be terminated at a main wiring harness where relatively clean ambient air can be sampled.

It is contemplated that the shape, size and configuration of the means for enhancing fluid communication may vary widely within the scope hereof. In general, it is only required that such means provide increased fluid communication between the interior and exterior space of the closed container. It has been found, however, that a channel or bore in the wall of the insulative sleeve of the present invention produces favorable results. In preferred embodiments, the electrical signal transmitting means comprises an elongate wire core, preferably a substantially cylindrical wire core, formed of conductive material, such as copper. The wire core may be solid but is preferably a braided wire cable or rope. In such embodiments, the insulating cover preferably comprises a sheath, preferably a generally tubular sheath, covering a substantial portion of the core. It will be appreciated that the end portions of the present lead wire will typically comprise uncovered core so as to facilitate electrical connection of the lead wire. That is, the insulating covering is typically stripped from the end of the lead wire. It is contemplated that the channel or bore in such embodiments may have various types and locations of entrance and exit ports and numerous cross sectional configurations. It is generally preferred, however, that the passageway comprise substantially cylindrical bore in the wall of the cover. It is also generally preferred that the longitudinal axis of the bore be substantially parallel to the axis of the elongate core. In such embodiments, the insulating cover of the lead wire has a gas entrance port in the external end wall thereof and a gas exit port in the internal end wall thereof.

The insulating cover is preferably comprised of a thermosetting or thermoforming plastic material, such as polytetrafluoroethylene and polyethylene, respectively. It is contemplated that other insulating plastic materials, such as polyamide and other polyolefins, are also suitable for use according to the present invention.

Figure 2:
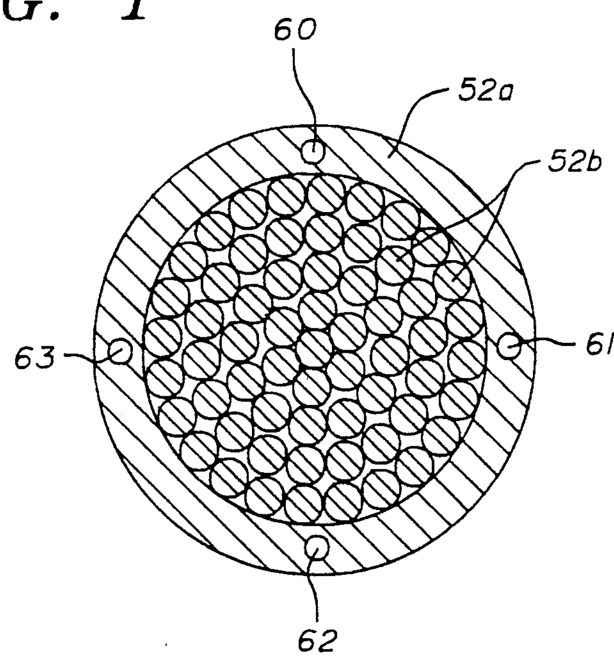
FIG. 2 is a cross-sectional view of an electrical heater lead taken substantially along lines 2—2 in FIG. 1.

With particular reference now to FIGS. 1 and 2, a simplified schematic sketch of an oxygen sensor and a cross section of a lead wire according to the present invention are illustrated. In particular, an oxygen sensor of the present invention, designated generally as 10, comprises a closed container 11. A wall portion 11*a* of the closed container is comprised of an ion-conducting material and is in the form of a cone depending from a lower portion of container 10. An upper wall portion of the closed container 10 includes a sealing member 11*b*, such as a grommet or sealing ring. An insulating cover 70 for the lead wires 50–53 is also provided.

The lead wires 50, 51, 52, and 53 comprise coverings 50*a*, 51*a*, 52*a*, and 53*a* and cores 50*b*, 51*b*, 52*b*, and 53*b*, respectively. The grommet 11*b* includes four access openings therein for substantially sealing engagement with the covers of the four lead wires 50, 51, 52 and 53. Grommet 11*b* is preferably comprised of resilient, nonporous material, and the access openings therein have outer diameters which are slightly smaller than the outer diameters of the insulated portions 50*a*, 51*a*, 52*a*, and 53*a* of the lead wires 50, 51, 52, and 53 respectively. Thus, there is a tight interference fit between the outer diameter of the lead wires 50–53 and the respective access openings in sealing member 11*b*, thus effectively minimizing or eliminating the flow of ambient air from the exterior of the closed container to the interior space thereof.

Disposed within the closed container 11 is heating element 16. Also contained completely within the container 11 is inner electrode 30, which is disposed on an inner surface of the ion-conductive wall portion 11*a*. In close and intimate contact with the lower portion of the closed container is outer electrode 32, which is disposed along an outer surface of the ion-conductive wall portion 11*a*. The heating element 16 comprises an outer metal sheath 16*a* which is closed at its lower end and within which a coaxial heating coil 40 is disposed. The upper end of coil 40 is welded to a coaxial inner rod 41. Coil 40 and inner rod 41 are electrically insulated from the outer sheath 16*a* in known fashion, for example, by way of ceramic insulation. The electrically conductive cores 50*b*–53*b* of lead wires 50–53 are attached to terminal portions in electrical communication with outer electrode 32, inner electrode 30, inner rod 41 and metal sheath 16*a*, respectively, thereby providing for the passage of electrical signals from within the closed container 10 to the exterior of the container, for example to an exterior pollution control system.

At least one of lead wires 50–53 includes means in the insulating cover thereof for enhancing fluid communication between the interior and exterior of the closed container 10. With particular reference to FIG. 2, the cross-sectional configuration of lead wire 52*a* is illustrated. The lead wire 52 comprises an inner core portion 52*b* surrounded by a plastic cover 52*a*. The core portion comprises numerous strands of copper wire braided into a substantially cylindrical wire rope or cable. The outer covering 52, which is preferably formed of polytetrafluoroethylene, contains four substantially cylindrical bores 60, 61, 62 and 63 within the wall thereof, the axis of each of such bores being substantially parallel to the axis of the core 52*b*. It will be appreciated by those skilled in the art that the particular number and spacing of the passageways according to the present invention can vary widely, and that the passageways shown in FIG. 2 are illustrative but not limiting of the present invention. Thus, it is contemplated that, according to certain embodiments, only a single passageway may be utilized. It will also be appreciated by those skilled in the art that the relative dimensions of the components of the lead wire will depend upon the particular application involved. In preferred embodiments, however, the insulating cover 52*a* has an inner diameter of about 0.049 inch and an outer diameter of about 0.091 inch. The bores 60–63 are located at about 90° apart and each has a diameter of about 0.007 inch.

Figure 3:
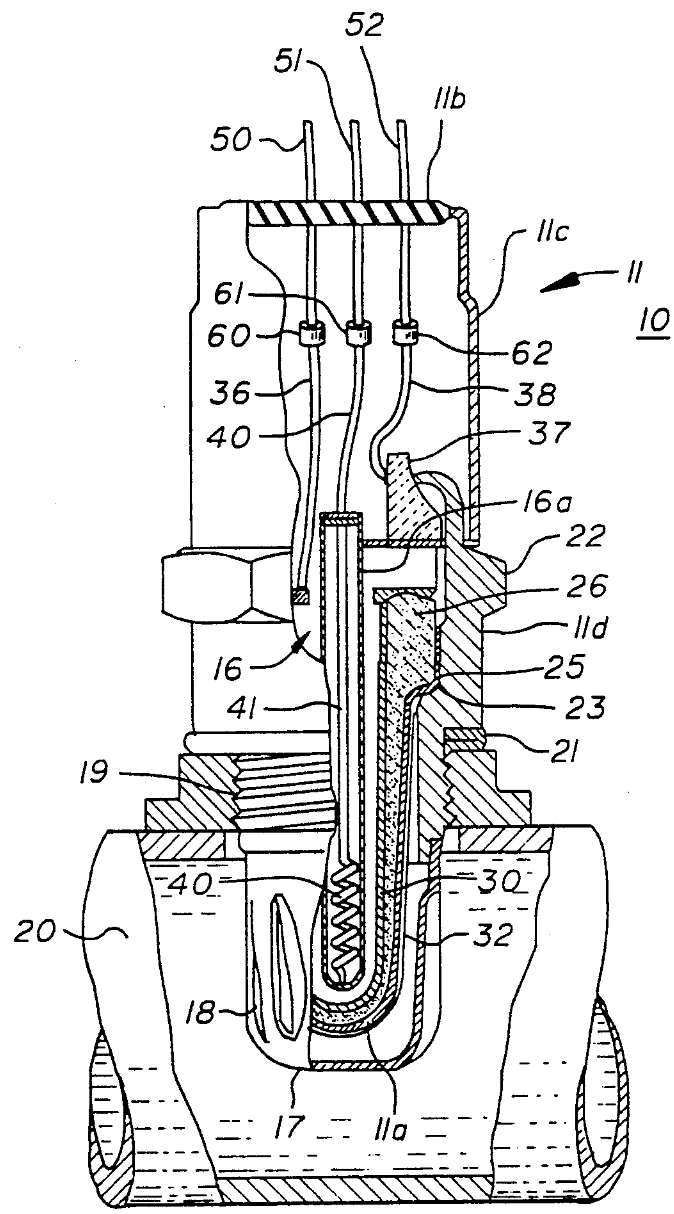
FIG. 3 is an elevation view in partial longitudinal section of a heated oxygen sensor made in accordance with a second embodiment of the present invention.

With reference now to FIG. 3, a second embodiment of an oxygen sensor according to the present invention is illustrated. For the purposes of convenience, similar or like components of the second embodiment are identified with the same reference numerals utilized in FIGS. 1 and 2.

The oxygen sensor of FIG. 3, designated generally as 10, comprises a closed container 11. The closed container 11 is formed by the joinder of the following wall portions: conically shaped wall portion 11*a*; sealing grommet 11*b*; upper casing 11*c*; and the upper portion of lower casing 11*d*. Each of these wall portions are joined according to well known techniques to provide a substantially closed container. The lower wall portion 11*a* comprises a cone shaped electrolyte tube formed of an oxygen-ion-conducting material. Disposed coaxially within the closed container 11 is a heater 16. A cup-shaped lower metal shield 17 depends from the lower end of casing 11*d*, thus surrounding the otherwise exposed lower end of the electrolyte tube 11*a*. Lower metal shield 17 has louvers 18 therein for allowing entry of exhaust gases. All of the aforementioned elements are provided in a substantially coaxial alignment in accordance with known techniques.

It is contemplated that the materials of construction of the present oxygen sensor may vary widely. It is generally required only that the closed container 11, the metal shield 17 and the other associated elements of the oxygen sensor are made of a material which will withstand the conditions of sensor use.

A lower portion of wall portion 11*d* has circumferential threads 19 for mounting the sensor in an automobile exhaust pipe 20. A soft annular gasket 21 is included above threads 19. Above gasket 21 is a hexagonal array of surface flats 22 for installing the oxygen sensor in the exhaust pipe 20. It will be appreciated that the sensor of the present invention is suitable for use in other components of an automotive exhaust system, such as the exhaust system manifold, tailpipe or special parallel exhaust passage.

On its inner surface, wall portion 11*d* has lower inward circumferential flange 23 which provides an annular sloped shoulder which in turn forms a tapered seat on which sealing ring 25 is disposed. Solid electrolyte tube 11*a* is tapered from its upper end to its closed lower end. The upper end has a larger diameter portion that forms a circumferential circular concentric flange 26. The wall thickness of the electrolyte tube 11*a* gradually decreases from flange 26 to the tube lower end. Flange 26 has a lower surface which forms a sloped shoulder generally similar in slope and configuration to the shoulder of the flange 23 of wall portion 11*d*. Lower metal sealing ring 25 thus provides a gas tight seal and low resistance electrical communication between wall portion 11*d* and wall portion 11*a*.

A first porous thick film platinum electrode 30 fully covers the bottom inner surface of electrolyte tube 11*a*. This inner electrode 30 serves as a reference electrode, in this case an air electrode for the sensor. A conductive strip-like coating, preferably of platinum paste, extends up the tube inner surface to the top of wall portion 11*a*.

A second porous thick platinum electrode 32 covers the outer surface of wall portion 11*a*. This outer electrode 32 serves as the exhaust gas electrode for the sensor. Outer platinum electrode 32 can be formed in the same manner as electrode 30. However, it may be more desirable to apply it by evaporation, sputtering or other such techniques. Outer electrode 32 is in low resistance electrical contact with wall portion 11*d* through the soft metal gasket 25. Hence, this electrode is in low resistance electrical communication with the closed container 11 and exhaust pipe 20.

The upper end of wall portion 11*c* is camphored on its periphery, forming a sloped shoulder having a container complimentary. The outer periphery sealing ring 11*b* has a complimentary contour. Inner electrode 30 and electrode terminal 36 are thus in low resistance electrical contact through the sealing ring 30. A slotted annular flange 37 is comprised of an electrically conductive material and is brazed or otherwise joined to both the outer casing 16*a* of heater 16 and the interior of the upper end of wall portion 11*d*. Thus, slotted annular flange 37 serves to coaxially align heater 16 with the closed container 11 and also to provide low resistance electrical connection between the outer casing 16*a* and the closed container 11. A terminal 38 is provided in electrical contact with a portion of flange 37, thus providing a ground terminal for the oxygen sensor.

Heater 16 includes a tubular outer metal sheath 16*a* closed at its lower end within which a coaxial heating coil 40 is disposed. The lower end of coil 40 is welded to the bottom of sheath 16*a*. The upper end of coil 40 is welded to a coaxial inner rod 41. Coil 40 and inner rod 41 are spaced form the outer sheath 16*a* in known fashion. The upper end of inner rod 41 thus provides a terminal for the electrical resistance heater 16.

In the embodiment of the oxygen sensor disclosed in FIG. 3, both the heater 16 and outer electrode 32 share a common electrical terminal, that is, ground terminal 38.

Terminals 36, 40 and 38 are electrically connected to the inner core of lead wires 50, 51 and 52, respectively, through low resistance electrical connectors 60, 61 and 62. An insulating spacer is provided to ensure that the core portions of the lead wires remain electrically isolated from one another.

Figure 4:
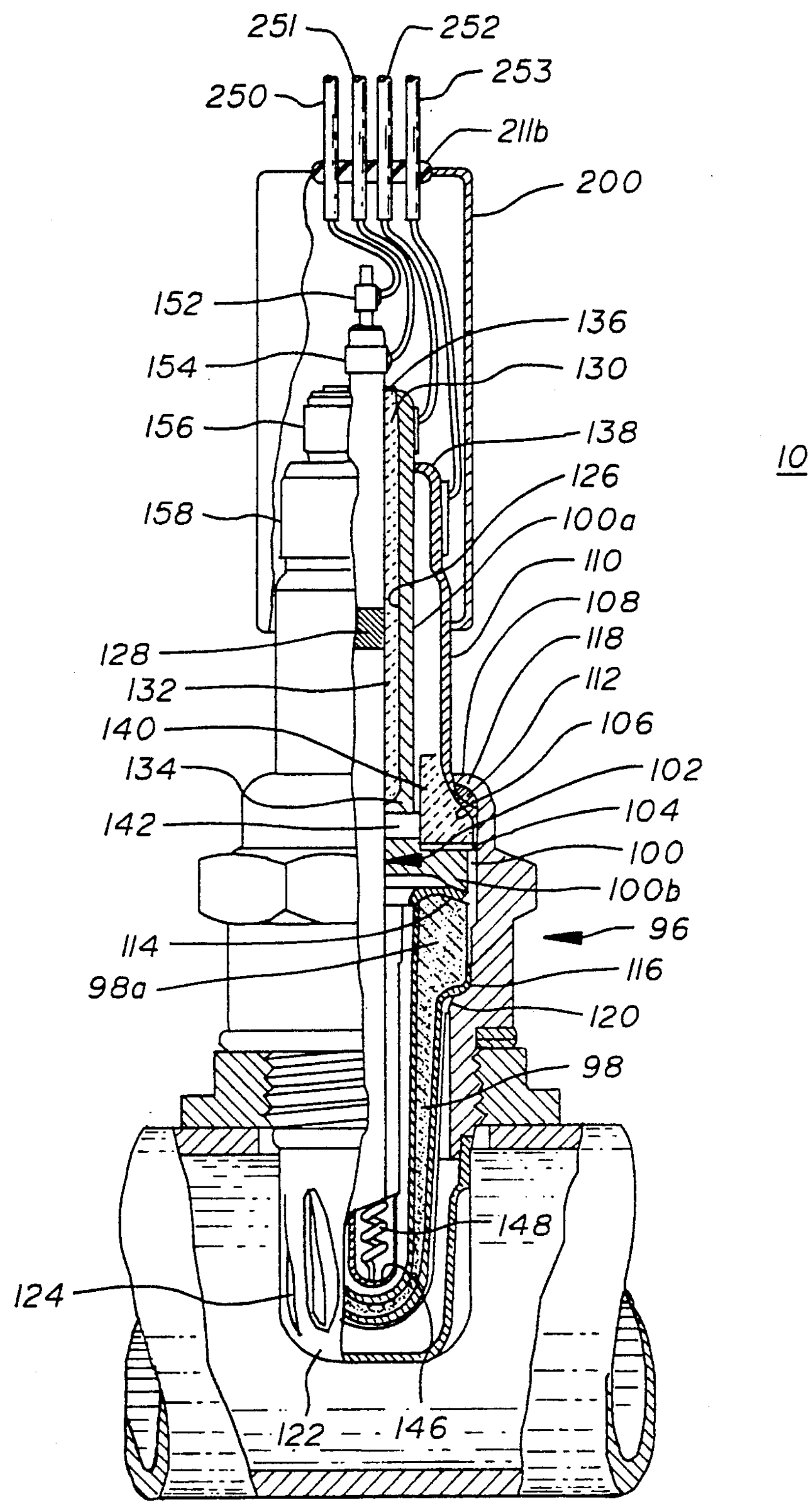
FIG. 4 is an elevation view in partial longitudinal section of the heated oxygen sensor made in accordance with the third embodiment of the present invention.

With reference now to FIG. 4, a third embodiment of an oxygen sensor according to the present invention is illustrated. The oxygen sensor of FIG. 4, designated generally as 10, is of the type disclosed in U.S. Pat. No. 4,175,019, which is incorporated herein in reference. According to such embodiments, the heater is electrically isolated from both sensor electrodes and their respective terminals.

The sensor of FIG. 4 includes a metal shell 96, a solid electrolyte tube 98, an electrode terminal member 100 and a heater 102, all coaxially aligned and with coaxial electrical terminal connection areas. The electrode terminal 100 has a central tubular portion 100*a* and circumferential flange 100*b*. Heater 102 is affixed to tubular portion 100*a* as will hereinafter be described. Above terminal flange 100*b* are successively a flat mica washer 104, a ceramic ring 106, a nested lower end flange 108 of an upper protective metal shield 110, and a soft steel metal gasket 112. Below flange 100*b* electrode terminal 100 is a soft metal sealing ring 114, a circumferential flange 98*a* on electrolyte tube 98 and a lower soft metal sealing ring 116. All of these components are compressed between an upper inward flange 118 and a lower inward flange 120 on shell 96. All of the foregoing components can be made of the same material and serve the same function as described in connection with the preceding embodiments of the present invention and as described in U.S. Pat. No. 4,175,019. Also, solid electrolyte tube 98 has inner and outer platinum coatings, as described hereinbefore. Shell 96 further has a lower metal shield 122 with openings 124 therein to permit entry of exhaust pipe gases.

Heater 102 is coaxially bonded with electroterminal tubular portion 100*a*, preferably by fused glass 126. As the term is used herein, fused glass means a body of glass that has been melted and resolidified in place, whereby the resolidified glass body adheres to surfaces it contacts. The outer surface of heater 102 is knurled at 128 to enhance bonding of the fused glass 126. Above and below fused glass 126, heater 102 is respectively spaced from electroterminal tubular portion 100*a* by an upper ceramic sleeve 130 and a lower ceramic sleeve 132. As can be seen, lower ceramic sleeve 132 is supported on the circumferential shoulder 134 on the inner surface of terminal tubular portion 100*a*. Ceramic sleeves 130 and 132 radially space heater 102 from the inner surface of electroterminal 100*b* along its entire length. This not only physically spaces heater 102 in terminal tube 100*b* apart but electrically isolates them. Fused glass 126 initially was a cylindrical body slightly longer than the spacing between ceramic sleeves 130 and 132 shown in the drawing. The glass cylinder and sleeves 130 and 132 are assembled in tube 100*a* with sleeve 130 projecting slightly beyond the end face 136 of terminal tubular portion 100*a*. Heater 102 is properly axially positioned within them. The glass cylinder is then melted in upper ceramic sleeve 130 moved inwardly into the position shown in the drawing. As a result, the molten glass completely fills an annular region between knurled portion 128 and the radially adjacent terminal tubular portion 100*a*. Concurrently, portions of the molten glass are also axially displaced along a short distance along the inner and outer surfaces of the adjacent ends of the ceramic sleeves. Along this distance, the molten glass fills the space between the sleeves and the heater 102 and the tube 100*a* at least at the sleeve inner ends. The molten glass is then cooled, so that it solidifies and bonds to heater 102, terminal tubular portion 100*a*, and ceramic sleeves 130 and 132. The glass also provides a seal. Its composition is not critical. Any glass can be used that melts at a temperature expected for the device and a temperature deleteriously affecting the heater or terminal materials such as their melting or cintering temperatures.

Solid electrolyte tube 98 has an outer platinum coating which is in low resistance electrical communication with upper shield 110. Electroterminal 100 is in low resistance electrical communication with a porous platinum electrode on the inner surface of electrolyte tube 98. Heater 102 includes an outer metal sheath closed at its lower end that encloses a coaxial helical resistance heating element 148 and a coaxial metal rod. The lower end of the resistance heating element 148 is welded to the closed end of sheath 146. The upper end of heating element 148 is welded to the lower end of a metal rod, and both are spaced from the surrounding metal sheath 146 by ceramic insulation, as for example, powdered magnesium.

The heated sensor of FIG. 4 thus has progressively larger silver-plated terminal connections at 152, 154, 156 and 158. The innermost two terminal connections 152 and 154 are for applying a heating voltage across element 148. The outermost two terminal connections 156 and 158 are for obtaining an output voltage from platinum electrodes on the inner and outer faces of electrolyte tube 98.

A closed container is formed by the sealed juncture between casing 200 and casing 110. An upper wall portion of the casing 200 includes a sealing member 211*b*, such as a grommet or sealing ring.

The lead wires 250, 251, 252 and 253 comprise coverings and cores as described in connection with FIG. 1. The grommet 211*b* includes four openings therein for substantially sealing engagement with the covers of the four lead wires 250, 251, 252 and 253. Grommet 211*b* is preferably comprised of resilient, non-porous material, and the access openings therein have outer diameters which are slightly smaller than the outer diameters of the insulated portions of the lead wires 250, 251, 252 and 253. Thus, there is a tight interface fit between the outer diameter of the lead wires 250–253 and the respective access openings in the sealing member 211*b*, thus effectively minimizing or eliminating the flow of ambient air from the exterior of the closed container to the interior space thereof.

The electrically conductive cores of lead wires 250–253 are attached to terminal portions of electrodes 152, 154, 156 and 158, respectively, thereby providing for the passage of electrical signals from within the closed container to the exterior of the container, for example, to an exterior pollution control system. Air which enters the closed container via the passageways in the insulating covers of lead wires 250–253, respectively, enters the sensor apparatus through an annular opening 138 in the upper end of shield 110. It passes down through shield 110 to an upper narrow generally annular passage 140 between ceramic ring 106 and electroterminal tubular portion 100*a*. A clearance of approximately 0.0005–0.01 inch between the outer diameter of tube 100*a* and the inner diameter of ceramic ring 106 provides the annual passage 140. Air entering annular passage 140 passes downwardly to aperture 142 in the lower wall of tube 100*a*, and through aperture 142 to a lower narrow generally annular passage between heater 102 and the lower end of terminal tube 100*b*. A passage of about 0.005–0.01 inch between the inner diameter of the tube 100*b* and the outer diameter of heater 102 provides the lower annular passage. Air then passes into the interior of electrolyte tube 98, where it contacts the inner electrode. Thus, the interior of the electrolyte tube 98 communicates with outside air through a baffled passage, further protecting it from particulate contaminants.

Those skilled in the art will appreciate that the foregoing is illustrative of the present invention, but not limiting thereof. Rather, the full scope of the present invention is defined solely with respect to the claims which follow.

What is claimed is:

1. A lead wire for use in connection with a heated solid electrolyte oxygen sensor having a substantially hermetically closed container, the lead wire comprising:

(a) an elongate, electrically conductive substantially cylindrical wire core; and (b) an electrically insulating tubular cover for said core, said tubular cover comprising fluorocarbon resin and a substantially cylindrical bore in the wall thereof for providing passage of air from the exterior of the container to the interior of the container, the longitudinal axis of said bore being substantially parallel to the longitudinal axis of said core.

2. The lead wire of claim 1 wherein said fluorocarbon resin comprises polytetrafluoroethylene.

3. The lead wire of claim 1 wherein said channel comprises four (4) substantially cylindrical bores in the wall of said tubular cover.

4. The lead wire of claim 3 wherein said bores are equally circumferentially spaced.

5. A lead wire for use in connection with an electrically heated oxygen sensor having a substantially closed container, the lead wire comprising:

(a) a conductive core for providing electrical communication between the interior and the exterior of the container;

(b) an insulating plastic member substantially surrounding said core; and (c) passage means in said plastic member for providing fluid communication between the interior of the container and the exterior of the container.

6. The lead wire of claim 5 wherein said means for providing fluid communication comprises a bore in a wall of said plastic member.

7. The lead wire of claim 6 wherein said insulating plastic member comprises a tubular cover.

8. The lead wire of claim 6 wherein said plastic member comprises a resin of fluorocarbon polymer.

9. A lead wire for use in connection with an oxygen sensor including a substantially closed container, the lead wire comprising:

(a) an electrically conductive core for providing electrical communication between the interior of the closed container and the exterior of the closed container; and (b) an insulating cover for said core, said cover comprising a wall portion having passage means for providing fluid communication between the interior of the container and the exterior of the container.

10. The lead wire of claim 9 wherein said passage means comprises a bore in said wall portion.

11. The lead wire of claim 10 wherein said bore is a substantially cylindrical bore.

12. The lead wire of claim 9 wherein said conductive core is a substantially cylindrical conductive core and wherein said passage means comprises a bore in said wall portion of said insulating cover.

13. The lead wire of claim 12 wherein the axis of said core is substantially parallel to the axis of said bore.

14. The lead wire of claim 9 wherein said insulating cover is a plastic cover formed from a fluorocarbon polymer resin.

15. The lead wire of claim 9 wherein said insulating cover is a plastic cover.

* * * * *